US012672870B2

(12) United States Patent (10) Patent No.: US 12,672,870 B2
Baxter, III et al. (45) Date of Patent: Jul. 7, 2026

(54) SURGICAL STAPLER CARTRIDGE WITH SUPPORT FEATURES

(71) Applicant: Cilag GmbH International, Zug (CH)

(72) Inventors: Chester O. Baxter, III, Loveland, OH (US); Michael J. Stokes, Cincinnati, OH (US); Shannon L. Jones, Cincinnati, OH (US); Gregory J. Bakos, Mason, OH (US); Sudhir Patel, Cincinnati, OH (US); Jason L Harris, Lebanon, OH (US); Laura S. Downing, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 417 days.

(21) Appl. No.: 17/951,612

(22) Filed: Sep. 23, 2022

(65) Prior Publication Data

US 2023/0309996 A1 Oct. 5, 2023

(30) Foreign Application Priority Data

Mar. 29, 2022 (IN) .............................. 202211018497

(51) Int. Cl.
*A61B 17/072* (2006.01)
*A61B 17/00* (2006.01)

(52) U.S. Cl.
CPC .. *A61B 17/072* (2013.01); *A61B 2017/00473* (2013.01); *A61B 2017/00526* (2013.01);
(Continued)

(58) Field of Classification Search
CPC ............ A61B 17/072; A61B 17/07207; A61B 2017/00473; A61B 2017/00526;
(Continued)

(56) References Cited

U.S. PATENT DOCUMENTS 4,568,009 A * 2/1986 Green .................. A61B 17/072
227/19
5,405,072 A * 4/1995 Zlock ............... A61B 17/07207
227/19
(Continued)

FOREIGN PATENT DOCUMENTS

EP 3120781 A2 1/2017
EP 3202337 A1 8/2017
EP 3730069 A1 10/2020

OTHER PUBLICATIONS

International Search Report and Written Opinion dated Jun. 15, 2023 for Application No. PCT/IB2023/053083, 15 pgs.
(Continued)

*Primary Examiner* — Shelley M Self
*Assistant Examiner* — Eduardo R Ferrero
(74) *Attorney, Agent, or Firm* — FBT Gibbons LLP

(57) ABSTRACT

An apparatus includes a first stapling assembly, a plurality of staples a plurality of staple drivers, and a second stapling assembly portion. The first stapling assembly portion has a deck surface defining a plurality of apertures. The staple drivers can drive the plurality of staples through the staple apertures of the deck surface. The second stapling assembly can couple with the first stapling assembly portion. The second stapling assembly portion has a section that overlies the deck surface. At least one of the first or second stapling assembly portions include a first support feature that inhibits deflection of the deck surface during stapling.

19 Claims, 16 Drawing Sheets

(52) U.S. Cl.
    CPC ............... *A61B 2017/07257* (2013.01); *A61B 2017/07271* (2013.01); *A61B 2017/07278* (2013.01); *A61B 2017/07285* (2013.01)

(58) Field of Classification Search
    CPC ........... A61B 2017/07257; A61B 2017/07271; A61B 2017/07278; A61B 2017/07285; A61B 17/07292; B33Y 80/00
    See application file for complete search history.

(56) References Cited

U.S. PATENT DOCUMENTS

| | | | |
|---|---|---|---|
| 7,404,508 B2 | 7/2008 | Smith et al. | |
| 7,434,715 B2 | 10/2008 | Shelton, IV et al. | |
| 7,721,930 B2 | 5/2010 | McKenna et al. | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 8,800,838 B2 | 8/2014 | Shelton, IV | |
| 9,131,940 B2 | 9/2015 | Huitema et al. | |
| 9,186,142 B2 | 11/2015 | Fanelli et al. | |
| 9,517,065 B2 | 12/2016 | Simms et al. | |
| 9,622,746 B2 | 4/2017 | Simms et al. | |
| 9,717,497 B2 | 8/2017 | Zerkle et al. | |
| 9,724,095 B2 * | 8/2017 | Gupta ................ | A61B 17/0682 |
| 9,795,379 B2 | 10/2017 | Leimbach et al. | |
| 9,808,248 B2 | 11/2017 | Hoffman | |
| 10,092,292 B2 | 10/2018 | Boudreaux et al. | |
| 10,123,798 B2 * | 11/2018 | Baxter, III ......... | A61B 17/0643 |
| 10,363,035 B2 * | 7/2019 | Harris .............. | A61B 17/07207 |
| 10,709,452 B2 | 7/2020 | DiNardo et al. | |
| 10,835,247 B2 * | 11/2020 | Shelton, IV ..... | A61B 17/07292 |
| 11,045,193 B2 | 6/2021 | Schings et al. | |
| 11,266,403 B2 | 3/2022 | Simms | |
| 11,432,815 B2 | 9/2022 | Courtwright et al. | |
| 11,517,325 B2 * | 12/2022 | Shelton, IV ........... | A61B 34/76 |
| 11,723,669 B2 * | 8/2023 | Thomas ............. | A61B 17/1285 |
| | | | 606/142 |
| 12,082,811 B2 * | 9/2024 | Fanelli ............. | A61B 17/07207 |
| 2006/0016853 A1 * | 1/2006 | Racenet ........... | A61B 17/07207 |
| | | | 227/176.1 |
| 2007/0083233 A1 * | 4/2007 | Ortiz ................ | A61B 17/07207 |
| | | | 227/176.1 |
| 2007/0114261 A1 * | 5/2007 | Ortiz ................ | A61B 17/07207 |
| | | | 227/175.1 |
| 2011/0121050 A1 * | 5/2011 | Nicholas .......... | A61B 17/07207 |
| | | | 227/175.1 |
| 2012/0018326 A1 * | 1/2012 | Racenet .......... | A61B 17/07207 |
| | | | 206/339 |
| 2012/0080493 A1 * | 4/2012 | Shelton, IV ..... | A61B 17/00491 |
| | | | 227/176.1 |
| 2012/0080501 A1 * | 4/2012 | Morgan ............. | A61B 17/2909 |
| | | | 227/180.1 |
| 2012/0132663 A1 * | 5/2012 | Kasvikis .............. | A61B 17/068 |
| | | | 220/694 |
| 2013/0068816 A1 * | 3/2013 | Mandakolathur Vasudevan ......... A61B 17/07292 |
| | | | 227/175.1 |
| 2013/0075448 A1 * | 3/2013 | Schmid ............ | A61B 17/07207 |
| | | | 227/176.1 |
| 2013/0161374 A1 * | 6/2013 | Swayze ............ | A61B 17/07292 |
| | | | 227/176.1 |
| 2014/0005679 A1 * | 1/2014 | Shelton, IV ......... | A61B 17/068 |
| | | | 606/130 |
| 2014/0239037 A1 * | 8/2014 | Boudreaux ...... | A61B 17/07207 |
| | | | 227/175.1 |
| 2014/0263546 A1 * | 9/2014 | Aranyi ............. | A61B 17/07207 |
| | | | 227/175.2 |
| 2015/0297236 A1 * | 10/2015 | Harris .................. | A61B 17/068 |
| | | | 227/176.1 |
| 2016/0058441 A1 * | 3/2016 | Morgan ............. | A61B 17/0644 |
| | | | 606/219 |
| 2016/0157876 A1 * | 6/2016 | Kim ...................... | A61B 17/30 |
| | | | 606/207 |
| 2018/0168616 A1 * | 6/2018 | Shelton, IV ........... | A61B 34/30 |
| 2018/0206844 A1 * | 7/2018 | Harris .............. | A61B 17/07292 |
| 2019/0290267 A1 * | 9/2019 | Baxter, III .......... | A61B 17/072 |
| 2020/0323526 A1 * | 10/2020 | Huang ............. | A61B 17/07207 |
| 2020/0337701 A1 * | 10/2020 | Campbell ........ | A61B 17/07207 |
| 2022/0133306 A1 * | 5/2022 | Nalagatla ......... | A61B 17/07207 |
| | | | 227/175.1 |
| 2022/0142642 A1 * | 5/2022 | de Maillé ........... | A61B 17/072 |
| 2023/0051305 A1 | 2/2023 | Jones et al. | |
| 2023/0309991 A1 | 10/2023 | Schings et al. | |

OTHER PUBLICATIONS

International Search Report and Written Opinion dated Sep. 8, 2023 for Application No. PCT/IB2023/053078, 18 pgs.

\* cited by examiner

SURGICAL STAPLER CARTRIDGE WITH SUPPORT FEATURES

PRIORITY

This application claims priority to Indian Provisional Pat. App. No. 202211018497, entitled "Surgical Stapler Cartridge with Support Features," filed on Mar. 29, 2022.

BACKGROUND

Examples of surgical instruments include surgical staplers, which may be configured for use in laparoscopic surgical procedures and/or open surgical procedures. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein in its entirety.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
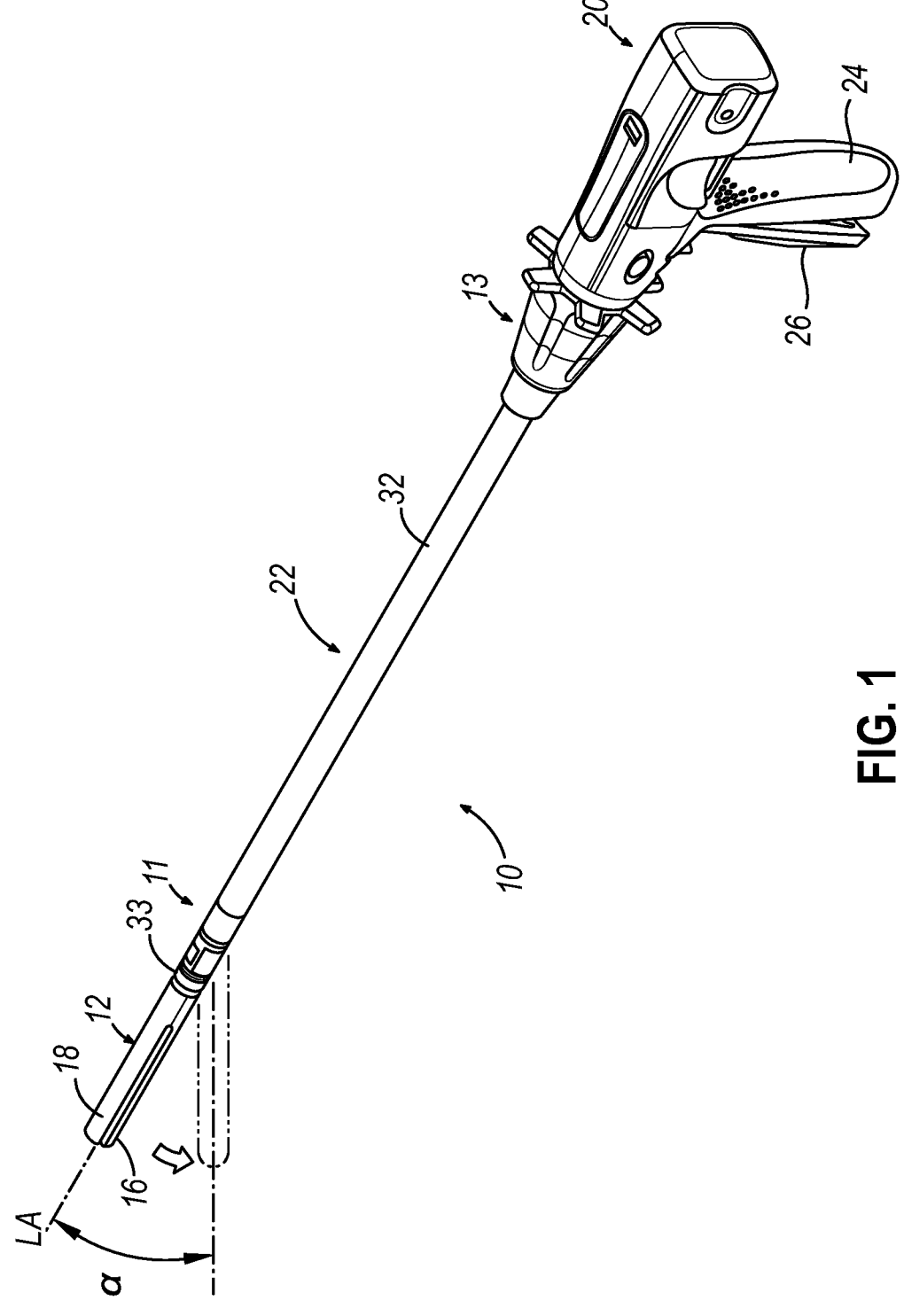
FIG. 1 depicts a perspective view of an example of an articulating surgical stapling instrument.
Figure 2:
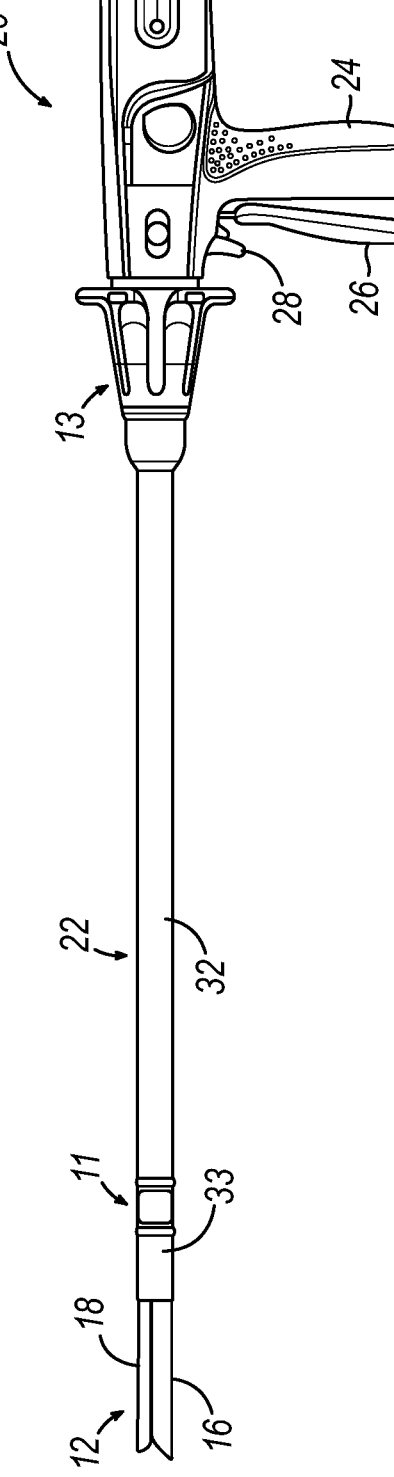
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an example of a surgical stapling and severing instrument (10) that is sized for insertion, in a nonarticulated state as depicted in FIG. 1, through a trocar cannula, thoracotomy, or other incision to a surgical site in a patient for performing a surgical procedure. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20).

Once articulation joint (11) and end effector (12) are inserted into the patient, articulation joint (11) may be remotely articulated, as depicted in phantom in FIG. 1, by an articulation control (13), such that end effector (12) may be deflected from the longitudinal axis (LA) of shaft (22) at a desired angle (α). By way of example only, articulation joint (11) and/or articulation control (13) may be constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein in its entirety; and/or U.S. Pat. No. 9,795,379, entitled "Surgical Instrument with Multi-Diameter Shaft," issued Oct. 24, 2017, the disclosure of which is incorporated by reference herein in its entirety. Other suitable forms that articulation joint (11) and articulation control (13) may take will be apparent to those skilled in the art in view of the teachings herein.

End effector (12) of the present example includes a lower jaw (16) and an upper jaw in the form of a pivotable anvil (18). By way of example only, lower jaw (16) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (18) may be constructed and operable in accordance with at least some of the teachings of at least some of the teachings of U.S. Pat. No. 10,092,292, entitled "Staple Forming Features for Surgical Stapling Instrument," issued Oct. 9, 2018, the disclosure of which is incorporated by reference herein in its entirety. Other suitable forms that lower jaw (16) and anvil (18) may take will be apparent to those skilled in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of tissue clamped in end effector (12), as will be described in greater detail below. Thereafter, triggers (26, 28) may be released to release the tissue from end effector (12).

Figure 4A:
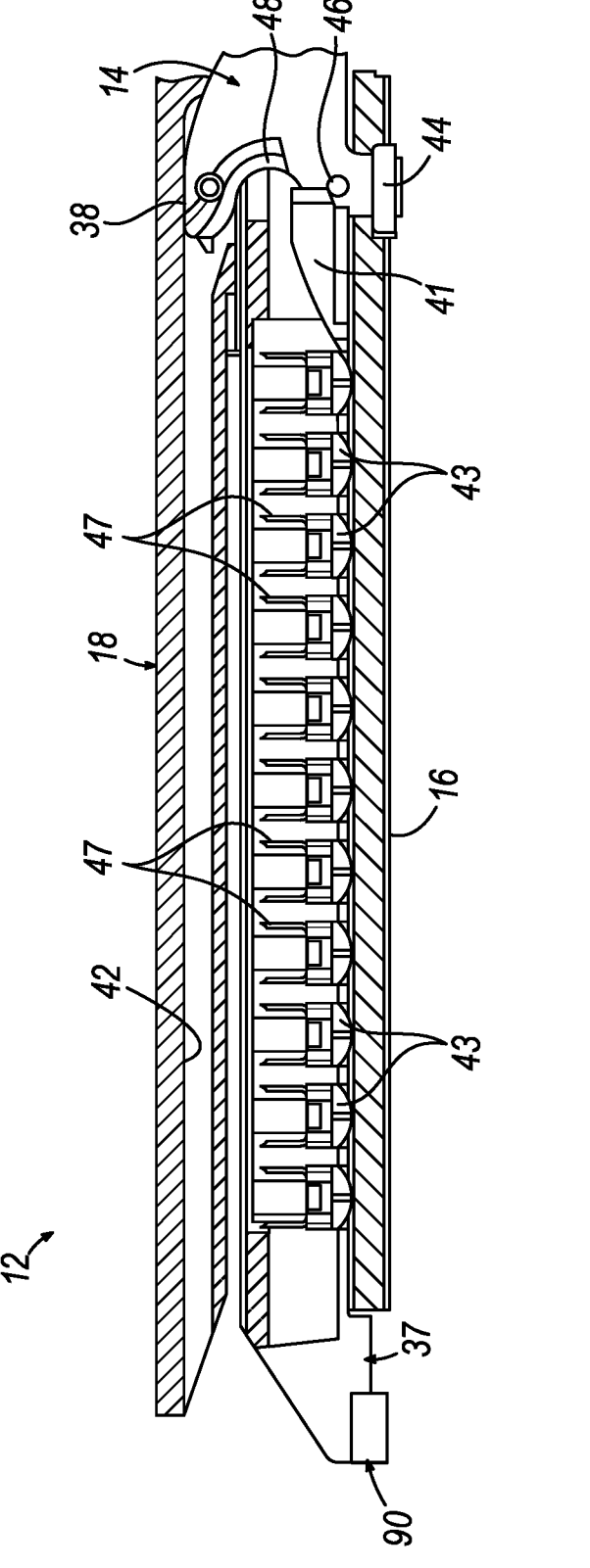
FIG. 4A depicts a side cross-sectional view of the end effector of FIG. 3, taken along line 4-4 of FIG. 3, with a firing beam in a proximal position.
Figure 4B:
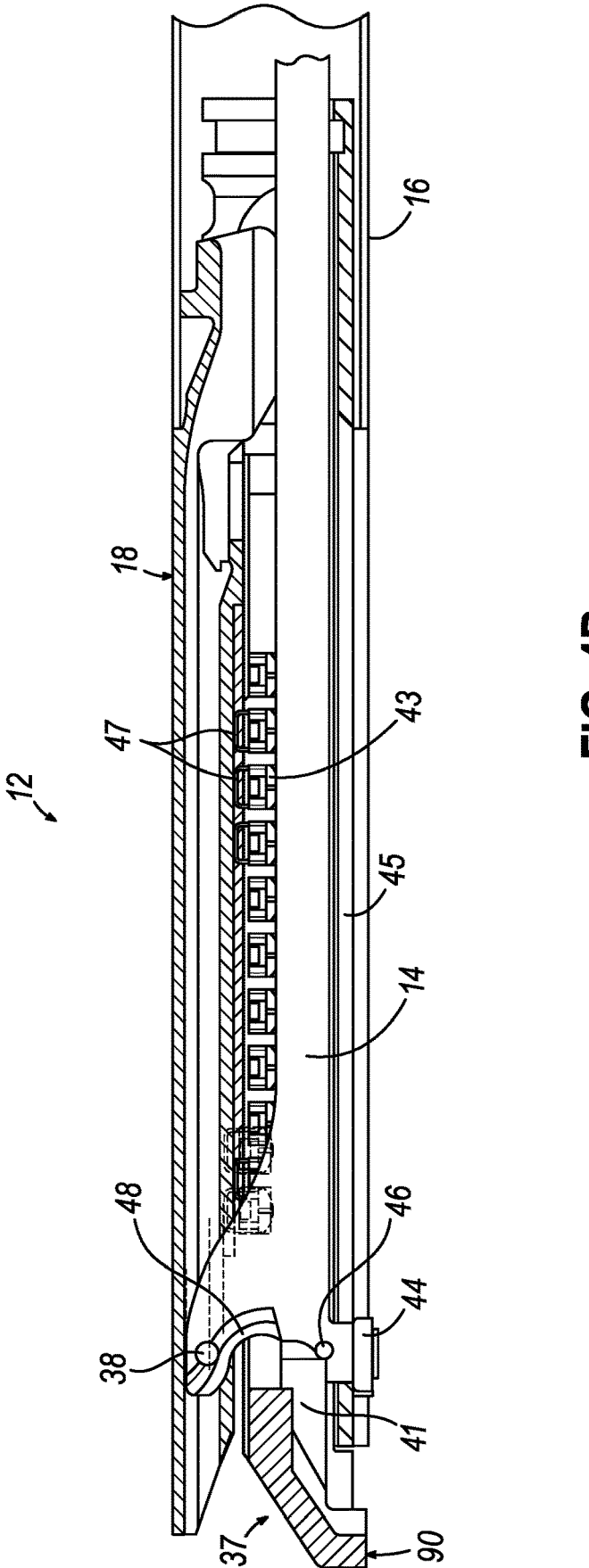
FIG. 4B depicts a side cross-sectional view of the end effector of FIG. 3, taken along line 4-4 of FIG. 3, with the firing beam in a distal position.

As best seen in FIGS. 4A-4B, firing beam (14) of the present example includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing. By way of example only, firing beam (14) and/or associated lockout features may be constructed and operable in accordance with at least some of the teachings of U.S. Pat. No. 9,717,497, entitled "Lockout Feature for Movable Cutting Member of Surgical Instrument," issued Aug. 1, 2017, the disclosure of which is incorporated by reference herein in its entirety. Other suitable forms that firing beam (14) may take will be apparent to those skilled in the art in view of the teachings herein.

Figure 3:
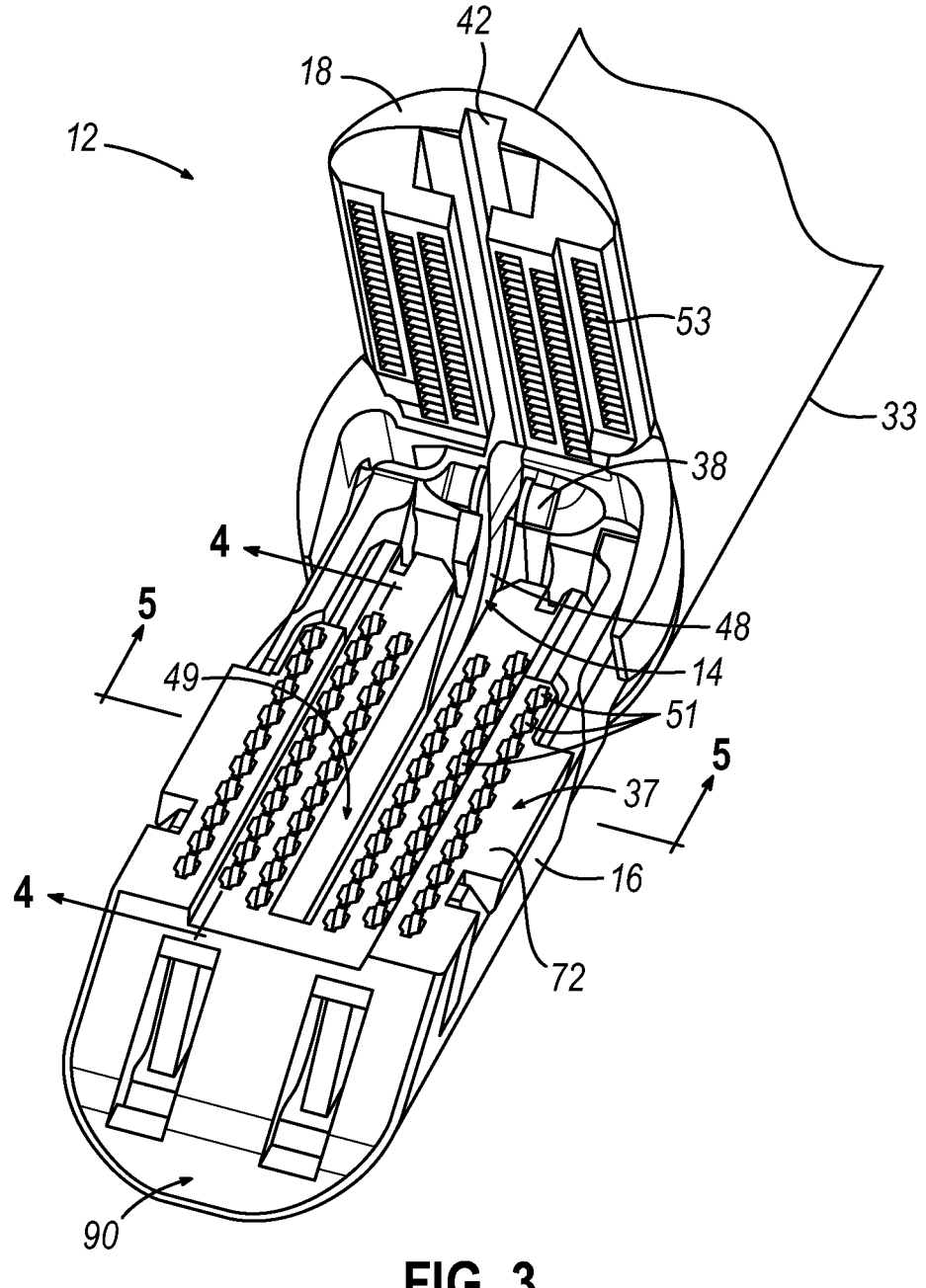
FIG. 3 depicts a perspective view of an opened end effector of the instrument of FIG. 1.
Figure 5:
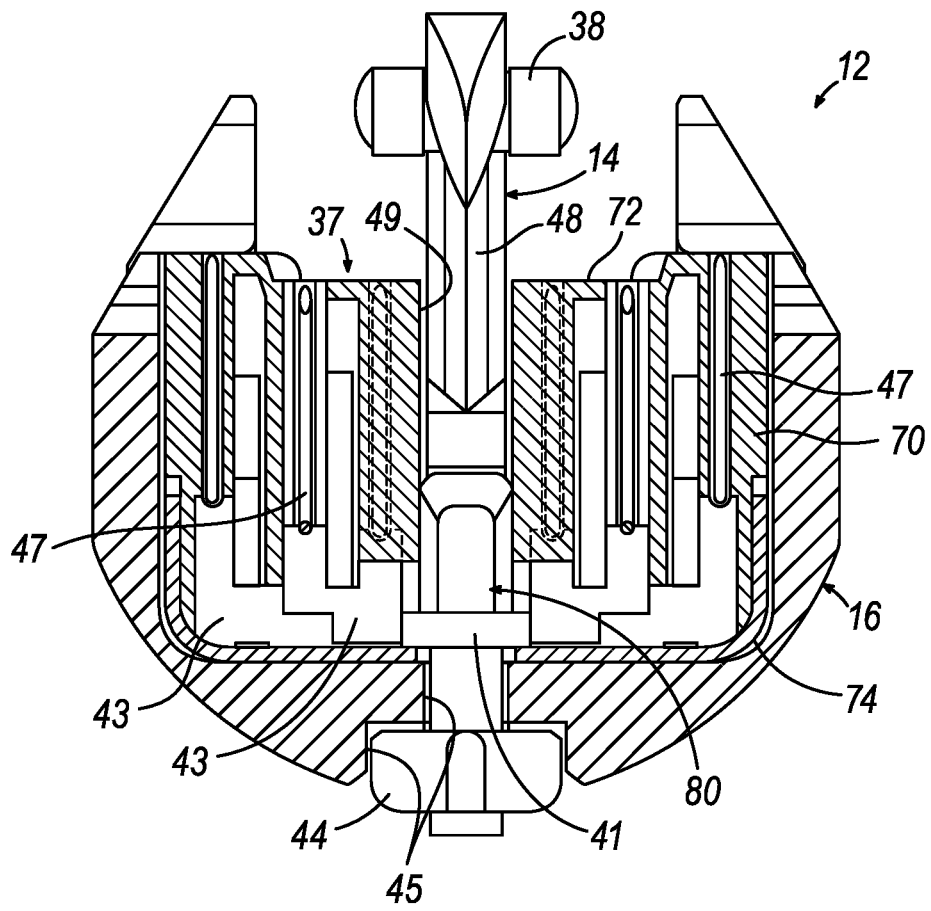
FIG. 5 depicts an end cross-sectional view of the end effector of FIG. 3, taken along line 5-5 of FIG. 3.
Figure 6:
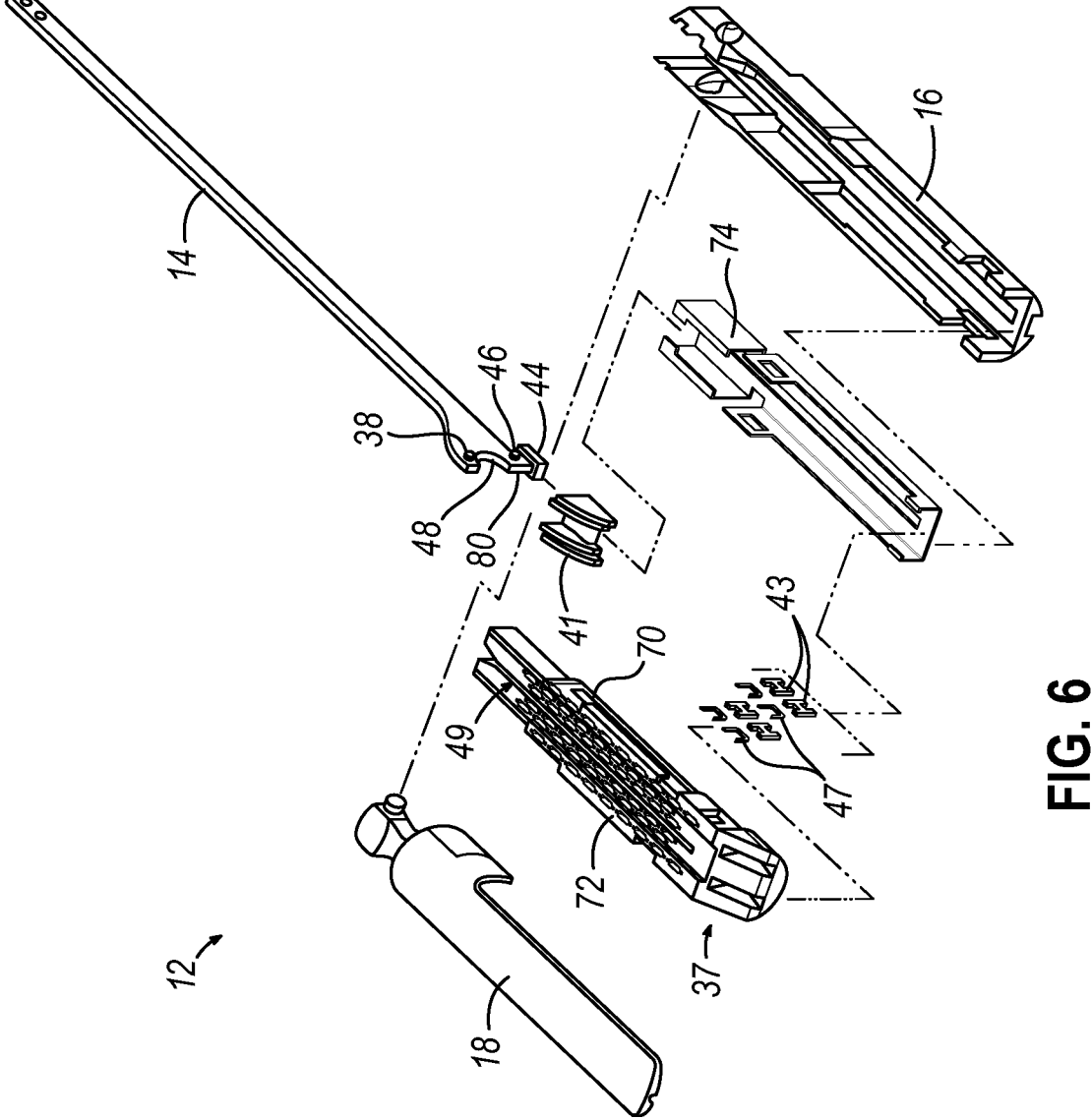
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). Three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43) when staple cartridge (37) is in a pre-fired (or "unspent") state. Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

By way of example only, staple cartridge (37) may be constructed and operable in accordance with at least some of the teachings of U.S. Pat. No. 9,517,065, entitled "Integrated Tissue Positioning and Jaw Alignment Features for Surgical Stapler," issued Dec. 13, 2016, the disclosure of which is incorporated by reference herein in its entirety. Other suitable forms that staple cartridge (37) may take will be apparent to those skilled in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) located at the distal end of firing beam (14) is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
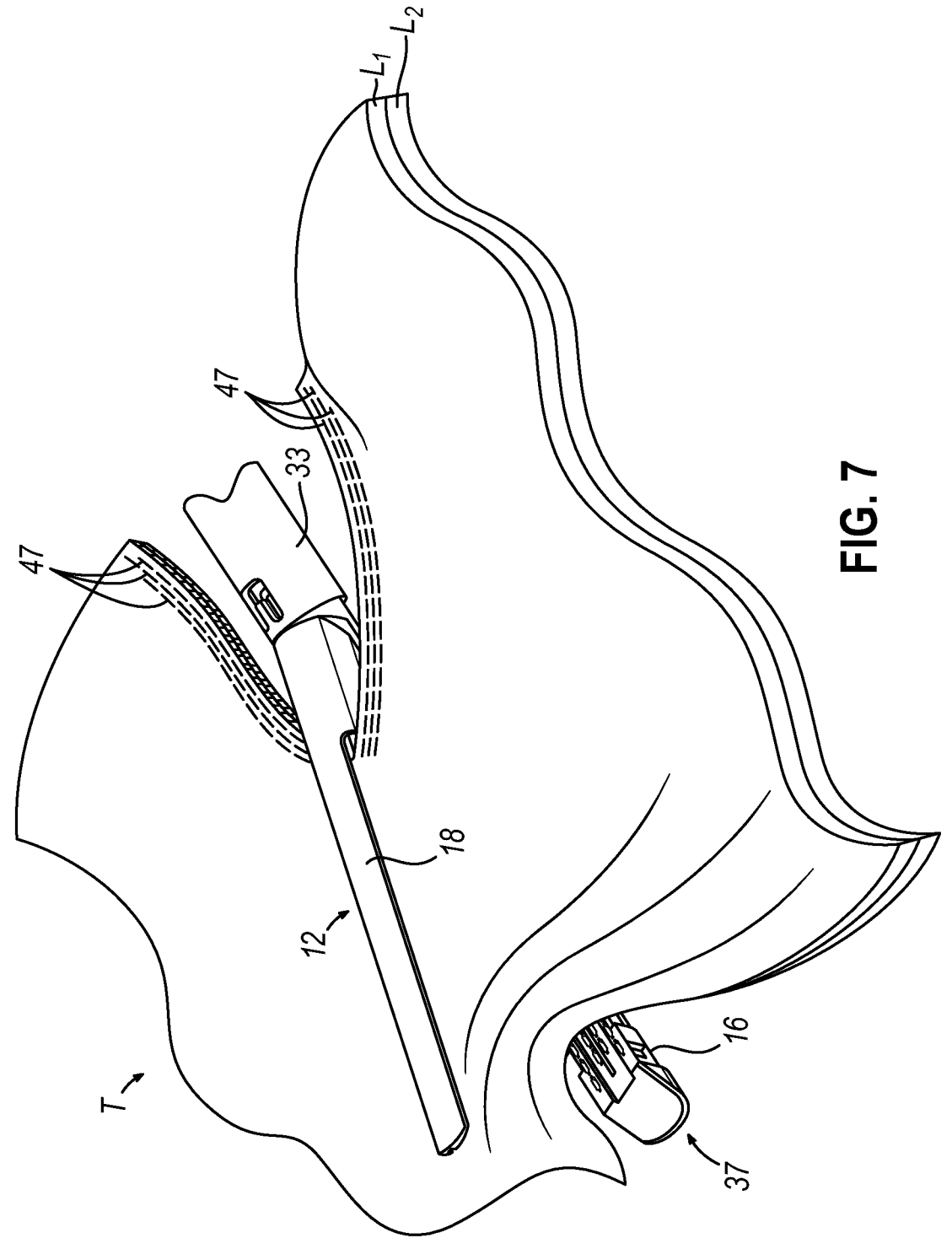
FIG. 7 depicts a perspective view of the end effector of FIG. 3, positioned at tissue and having been actuated once in the tissue.

FIG. 7 shows end effector (12) having been actuated through a single stroke through layers ($L_1$, $L_2$) of tissue (T). As shown, cutting edge (48) (obscured in FIG. 7) has cut through tissue (T), while staple drivers (43) have driven three alternating rows of staples (47) through the tissue (T) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar or incision after the first stroke is complete, spent staple cartridge (37) is replaced with a new staple cartridge, and end effector (12) is then again inserted through the trocar or incision to reach the stapling site for further cutting and stapling. This process may be repeated until the desired number of cuts and staples (47) have been provided. Anvil (18) may need to be closed to facilitate insertion and withdrawal through the trocar; and anvil (18) may need to be opened to facilitate replacement of staple cartridge (37).

In some versions, instrument (10) provides motorized control of firing beam (14). By way of example only, such motorization may be provided in accordance with at least some of the teachings of U.S. Pat. No. 9,622,746, entitled "Distal Tip Features for End Effector of Surgical Instrument," issued Apr. 18, 2017, the disclosure of which is incorporated by reference herein in its entirety; and/or U.S. Pat. No. 8,210,411, entitled "Motor-Driven Surgical Instrument," issued Jul. 3, 2012, the disclosure of which is incorporated by reference herein in its entirety. Other suitable components, features, and configurations for providing motorization of firing beam (14) will be apparent to those skilled in the art in view of the teachings herein. It should also be understood that some other versions may provide manual driving of firing beam (14), such that a motor may be omitted.

II. Exemplary Staple Cartridge with Support Features

As mentioned above, anvil (18) is configured to actuate relative to lower jaw (16). Anvil (18) may actuate toward lower jaw (16) such that the surface of anvil (18) defining pockets (53) grasps tissue in conjunction with upper deck (74) (sometimes referred and a "staple deck"). Additionally, as mentioned above, staple cartridge (37) includes cartridge body (70) and lower cartridge tray (74). Body (70) and tray (74) suitably contain wedge sled (41), staples (47), and staple drivers (43) such that body (70) suitably guides contained components along their intended firing path while tray (74) functions as a floor. In other words, body (70) suitably contains actuating components such that wedge sled (41) may translate longitudinally in order to actuate staple drivers (43) vertically to push staples (47) out of apertures (51) and against anvil (18) in accordance with the description herein. Therefore, during manufacturing and assembly, body (70) is manufactured to suitably define slot (49), apertures (51), and any other suitable cavities necessary to suitably housing sled (41), drivers (43), and staples (47) such that staples (47) are consistently and accurately fired against anvil (18) in accordance with the description herein. After body (70) is formed, movable components are then assembled within suitable cavities of body (70), and tray (74) is coupled to body (70) to keep movable components suitably housed within body (70).

In instances where a staple cartridge (37) is a prototype (e.g., a first, preliminary model), the use of mass-production manufacturing methods (such as expensive molds and other specialized equipment designed to efficiently mass produce a cartridge (37)) may not be readily available or economically viable. Without the use of mass-production manufacturing methods, the lead time for producing a prototype staple cartridge (37) may be longer than desirable. Therefore, it may be desirable to manufacture a prototype staple cartridge (37) in a fast and reliable manner.

One manufacturing method that allows for a fast lead time while producing prototype staple cartridges is 3D printing. However, in such instances, the material utilized in the 3D printing process or any other suitable prototype manufacturing process (e.g., Stereolithography (SLA)) may allow for fast and accurate manufacturing of a prototyped cartridge body (70), but may not provide sufficient structural integrity for use of a prototyped cartridge body (70) during exemplary use of end effector (12) in accordance with the description above. For example, a prototyped cartridge body (70) 3D printed with SLA material that may deflect, bend, or even break in response to end effector (12) grasping tissue (or tissue-like materials) in accordance with the description herein. Therefore, it may also be desirable to provide reinforcement features to a prototype staple cartridge (37) in order to inhibit undesirable consequences described herein. In some instances, it may be desirable to provide such reinforcement features to a staple cartridge body (70) that is formed by various other manufacturing methods as well, such as injection molding, to promote optimal rigidity and overall performance of the resulting staple cartridge (37) during use.

Figures 8, 8A:
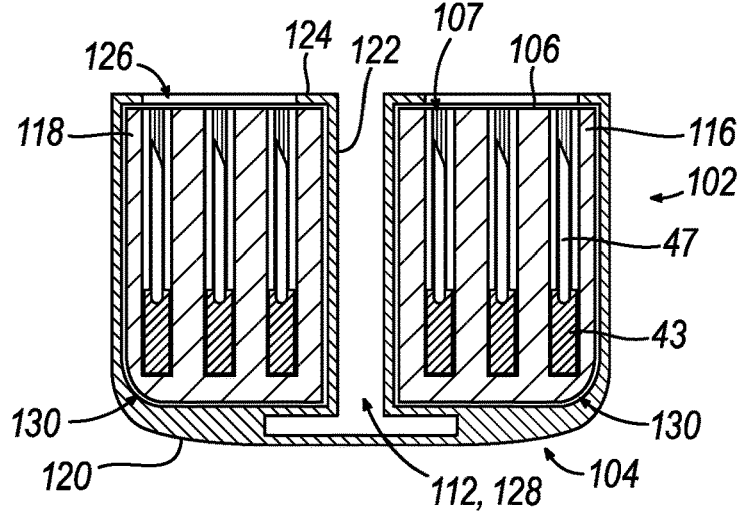
FIG. 8 depicts an exploded perspective view of an exemplary replaceable staple cartridge.
FIG. 8A depicts a front cross-sectional view of the replaceable staple cartridge of FIG. 8.

FIGS. 8-8A show an example staple cartridge assembly (100) that may be readily incorporated into end effector (12) in replacement of staple cartridge (37) described above. Staple cartridge assembly (100) includes a cartridge body (102) and a cartridge tray (104); which may be substantially similar to cartridge body (70) and lower cartridge tray (74) described above, with differences elaborated below. As will be described in greater detail below, cartridge body (102) is configured be longitudinally inserted into cartridge tray (104) in order to attached to tray (104). Having the ability to couple via longitudinal insertion may allow body (102) to be manufactured as a "straight pull" molded insert, which would make body (102) faster and cheaper to manufacture.

Additionally, cartridge body (102) may be formed utilizing a manufacturing process, such as 3D printing with SLA material, which has a relatively weaker/less-rigid construction than if formed via traditional manufacturing methods such as injection molding. Cartridge tray (104) includes support protrusions in the form of interior vertical legs (122), each having a respective top frame surface (124) that are configured to provide more stability and support as cartridge assembly (100) grasps tissue in conjunction with anvil (18) in accordance with the description herein, thereby inhibiting the relatively weaker material of body (102) from undesirably deforming or breaking during exemplary use.

Cartridge body (102) includes an upper deck (106) defining a plurality of staple apertures (107), which are substantially similar to upper deck (72) and staple apertures (51) described above, with differences elaborated below. Therefore, as shown in FIG. 8A, each aperture (107) slidingly contains a respective staple driver (43) and staple (47). A proximal end of cartridge body (102) has suitable openings for firing beam (14) of end effector (12) to suitably actuate a firing stroke through cartridge assembly (100).

Cartridge body (102) extends between a proximal end (108) and a distal end (110) having an atraumatic distal nose (114). Body (102) includes two longitudinally extending bodies (116, 118) that together define a vertical slot (112) such that each body (116, 118) includes a portion of deck (106). Vertical slot (112) extends proximally through proximal end (108) such that the proximal end of vertical slot (112) is open; while a distal end of vertical slot (112) adjacent to nose (114) is closed. Longitudinally extending bodies (116, 118) are sufficiently spaced apart from each other via vertical slot (112) such that each body (116, 118) may slidingly fit within a respective body channel (130) of tray (104). Body channels (130) extend between proximal end and distal end of tray (104) such that channels (130) have open ends on each side of tray (104). Therefore, proximal end of body (118, 116) may be suitably aligned with a distal end of tray (104) such that each body (116, 118) may slidingly fit within a respective body channel (130). Once suitably aligned, a user may slide bodies (116, 118) proximally into body channels (130). Open proximal end of slot (112) accommodates each body (116, 118) to be initially inserted within a respective body channel (130).

Allowing cartridge body (102) to initially coupled with tray (104) via longitudinal insertion may allow cartridge body (102) to be manufactured as a straight pull molded insert; which may save time and cost associated with manufacturing a prototype cartridge assembly (100). Alternatively, cartridge body (102) may be 3D printed or formed via any other suitably fast and efficient prototyping manufacturing method as would be apparent to one skilled in the art in view of the teachings herein.

Cartridge body (102) may be formed from a prototyping material that is easy to produce accurate dimensions in a fast and efficient manner, such as 3D printing with SLA materials. As mentioned above, use of such a material may not provide sufficient structural integrity to be used in accordance with the description herein. Therefore, tray (104) includes features that may support cartridge body (102) during exemplary use in accordance with the description herein.

Tray (104) includes a tray body (120) dimensioned to receive cartridge body (102) and selectively couple with lower jaw (16). Tray (104) may be formed of any suitable material that would be apparent to one skilled in the art in view of the teachings herein, such as a suitable metal material. The material forming tray (104) may be relatively thicker than the material forming tray (74) described above.

Tray body (120) is generally U-shaped. A pair of internal vertical legs (122) extend upwardly from the base of tray body (120) to define complementary vertical slot (128). Similar to vertical slot (49) of staple cartridge (37) described above, complementary vertical slot (128) is dimensioned to receive selected portions of firing beam (14) during the firing of end effector (12) in accordance with the description herein.

A top end of each leg (122) is coupled to a respective top frame surface (124). Top frame surface (124) extends between a respective interior leg (122) to a respective side wall of tray body (120). Top frame surface (124) defines a deck window (126) dimensioned to receives the portion of deck (106) defining apertures (107). Deck window (126) allows apertures (107) to face toward anvil (18) during example use without covering apertures (107), which would inhibit staples (47) from being fired against anvil (18). While one large deck window (126) is defined in the current example, this is merely optional. Any suitably number of deck windows (126) may be defined as would be apparent to one skilled in the art in view of the teachings herein. Windows (126) may have any suitable shape as would be apparent to one skilled in the art in view of the teachings herein.

Top frame surfaces (124) and legs (122) are dimensioned to distribute as least some of the load in response to cartridge assembly (100) grasping tissue onto tray body (120) such that an undesirable amount of the tissue grasping forces are not directly imparted on cartridge body (102). Frame surfaces (124), and legs (122) may also contribute to further stability of cartridge assembly (100) during exemplary use in accordance with the description herein. Therefore, in instances where cartridge body (102) is made from a prototyping material that may be prone to deformation, cracking, or breaking during exemplary use of end effector (12), top frame surfaces (124) and legs (122) may absorb at least some of the tissue grasping forces and distribute such forces onto tray body (120) to inhibit such undesirable consequences.

As a result, the structure of tray (104) may allow for cartridge body (102) to be manufactured with a prototyping material to provide a quick lead time for producing a prototype cartridge assembly (100). Additionally, the longitudinal insertion of body (102) into tray (104) may also allow cartridge assembly (100) to be manufactured using a straight pull molded insert method, which may also save time and costs in producing a prototype cartridge assembly (100).

FIGS. 9-11B show an example staple cartridge assembly (200) that may be readily incorporated into end effector (12) in replacement of staple cartridge (37) or staple cartridge assembly (100) described above. Staple cartridge assembly (200) includes a cartridge body (202) and a cartridge tray (204); which may be substantially similar to cartridge body (70) and lower cartridge tray (74) described above, with differences elaborated below. Similar to cartridge body (102) and tray (104) described above, cartridge body (202) is configured be longitudinally inserted into cartridge tray (204) in order to attach to tray (204). However, rather than having cartridge body (202) define staple deck and apertures, tray (204) includes staple deck (206) defining apertures (207). Staple deck (206) may function substantially similar to upper deck (74) described above, except staple deck (206) is a component of tray (204) rather than cartridge body (202). Tray (204) may be formed of a similar material to tray (104) described above. Tray (204) may be formed of a material that is thicker than the material used to form tray (74) described above.

Figures 9, 10:
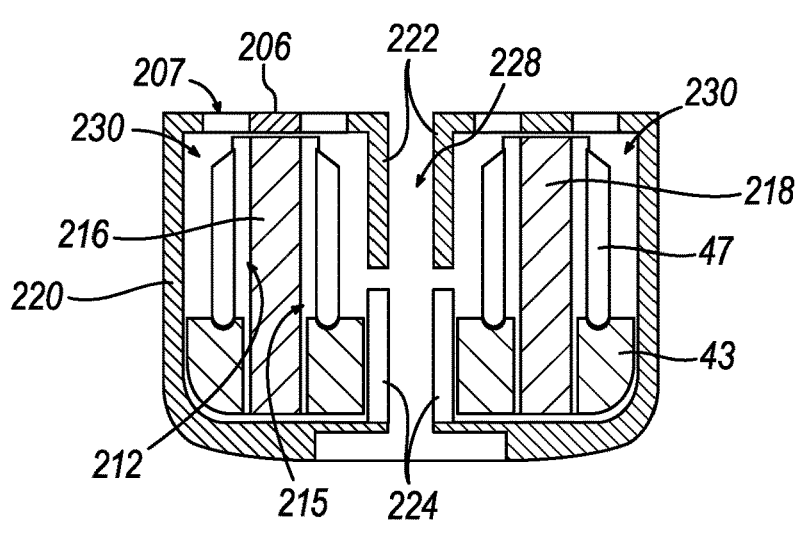
FIG. 9 depicts an exploded perspective view of another exemplary replaceable staple cartridge.
FIG. 10 depicts a front cross-sectional view of the replaceable staple cartridge of FIG. 9.

Cartridge body (202) includes two longitudinally extending bodies (216, 218) and a distal, atraumatic nose (214). Similar to bodies (116, 118) and channels (130) described above, bodies (216, 218) are dimensioned to be proximally inserted within a respective channel (230) of tray (204). Body channels (230) extend between proximal end and distal end of tray (204) such that channels (230) have open ends on each side of tray (204). However, rather than entirely housing staples (47) and staple drivers (43), longitudinally extending bodies (216, 218) each include an array of outwardly presented recesses (212) and inwardly presented recesses (215). As best shown in FIG. 10, recesses (212, 215) cooperate with U-shaped tray body (220), foldable support struts (224), and downwardly presented interior legs (222) of tray (204) in order to suitably house staple drivers (43) and staples (47). Therefore, portions of tray (204) replace the outer portions of cartridge body (202) in order to house staples (47) and drivers (43). Recesses (212, 215) are dimensioned to inhibit a respective driver (43) and staple (47) from undesirable longitudinal movement relative to cartridge body (202) and tray (204) once assembled. Utilizing recesses (212, 215) and portions of tray (204) to contain staples (47) and drivers (43) may provide better control of staples (47) and driver (43) during assembly, thereby allowing for faster and more efficient manufacturing times.

The simplified structure of cartridge body (202) may allow cartridge body (202) to be manufactured utilizing fast and cost-efficient prototyping methods, such as 3D printing and/or simplified molds. Alternatively, any other suitably fast and efficient prototyping manufacturing method as would be apparent to one skilled in the art in view of the teachings herein.

Tray (204) includes tray body (220). Unlike tray body (120) described above, tray body (220) includes staple deck (206) defining staple apertures (207). Therefore, staples (47) housed within the confines of recesses (212, 215) and portions of tray (204) may be actuated out of apertures (207) and toward anvil (18) in accordance with the description herein.

A pair downwardly presented interior legs (222) extends downward from staple deck (206) such that staple deck (206) and interior legs (222) help define vertical slot (228). Similar to vertical slot (128) described above, vertical slot (228) is dimensioned to receive selected portions of firing beam (14) during the firing of end effector (12) in accordance with the description herein.

Tray (204) also includes two arrays of foldable support struts (224) extending along the length of tray (204). The arrays of foldable support struts (224) are spaced apart from each other and each array is laterally aligned with a respective interior leg (222) such that struts (224) also help define a portion of vertical slot (228). In a pre-fired position (i.e., before end effector (12) is fired to drive staples (47) out of cartridge assembly (200)), interior legs (222) and respective foldable struts (224) are dimensioned to engage each other at their free-ends in response to cartridge assembly (200) grasping tissue with anvil (18). Therefore, interior legs (222) and foldable struts (224) function as support protrusions that may distribute as least some of the load in response to cartridge assembly (200) grasping tissue in accordance with the description herein onto tray body (220) such that an undesirable amount of the tissue grasping forces are not directly imparted on cartridge body (202). In instances where cartridge body (202) is made from a desirable prototyping material that may be prone to deformation, cracking, or breaking during exemplary use of end effector (12), interior legs (222) and foldable struts (224) may absorb at least some of the tissue grasping forces and distribute such forces onto tray body (220) to inhibit such undesirable consequences.

Figures 11A, 11B:
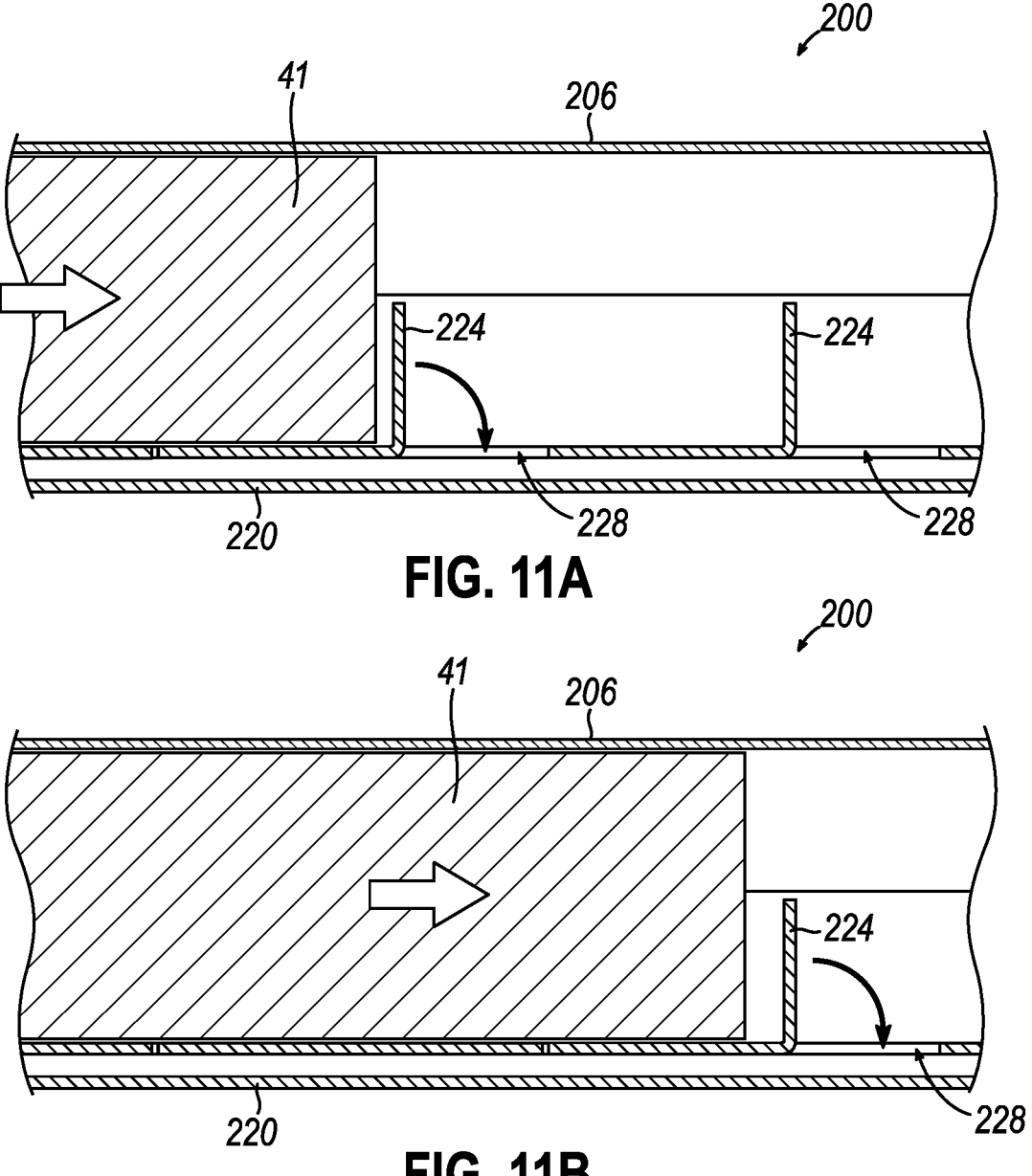
FIG. 11A depicts a side cross-sectional view of the replaceable staple cartridge of FIG. 9 with a wedge sled in a first firing position.
FIG. 11B depicts a side cross-sectional view of the replaceable staple cartridge of FIG. 9 with the wedge sled of FIG. 11A in a second firing position.

Foldable struts (224) are also configured to bend in response to wedge sled (41) actuating within channels (230) to drive staples (47) against anvil (18) in accordance with the description herein. Therefore, as shown in FIGS. 11A-11B, wedge sled (41) may be actuated within vertical slot (228) and both channels (230) to drive staples (47) against anvil (18). In response to longitudinal actuation of wedge sled (41), foldable struts (24) bend downward to allow wedge sled (41) to complete a firing stroke. Therefore, prior to firing end effector (12) with cartridge assembly (200), struts (224) and legs (222) may distribute as least some of the load through tray (204) in response to cartridge assembly (200) grasping tissue. Additionally, struts (224) may bend in order to allow wedge sled (41) to translate through tray (204) and suitably engage each staple driver (43) in accordance with the description herein.

As a result, the structure of tray (204) may allow for cartridge body (202) to be manufactured with a prototyping material to provide a quick lead time for producing a prototype cartridge assembly (200). Additionally, the longitudinal insertion of body (202) into tray (204) may also allow cartridge assembly (100) to be manufactured using a straight pull molded insert method, which may also save time and costs in producing a prototype cartridge assembly (200).

It should be understood that tray (104) described above may incorporate foldable struts (224) and interior legs (222) in order to distribute tissue grasping loads and accommodate the firing of wedge sled (41) in similar fashion to cartridge assembly (200) described herein.

Figure 12:
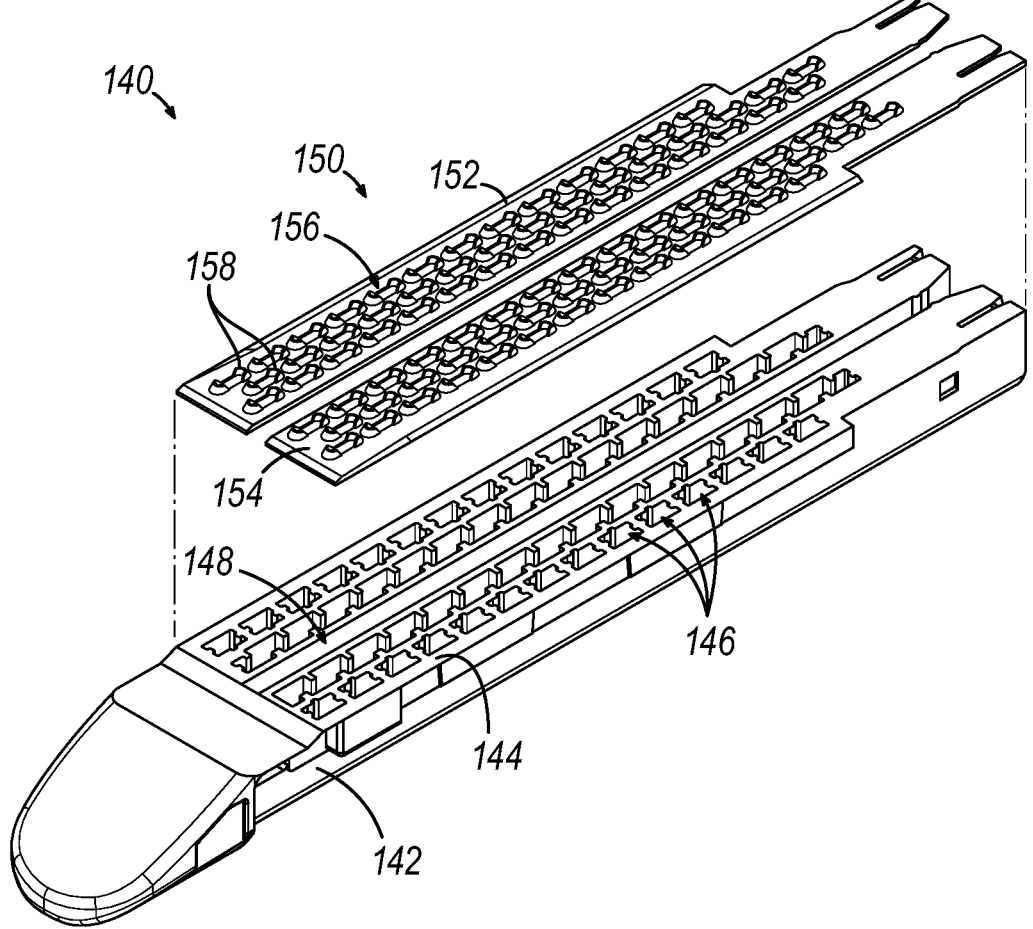
FIG. 12 depicts an exploded perspective view of an exemplary staple cartridge having a 3D printed body and a metal deck.
Figure 13:
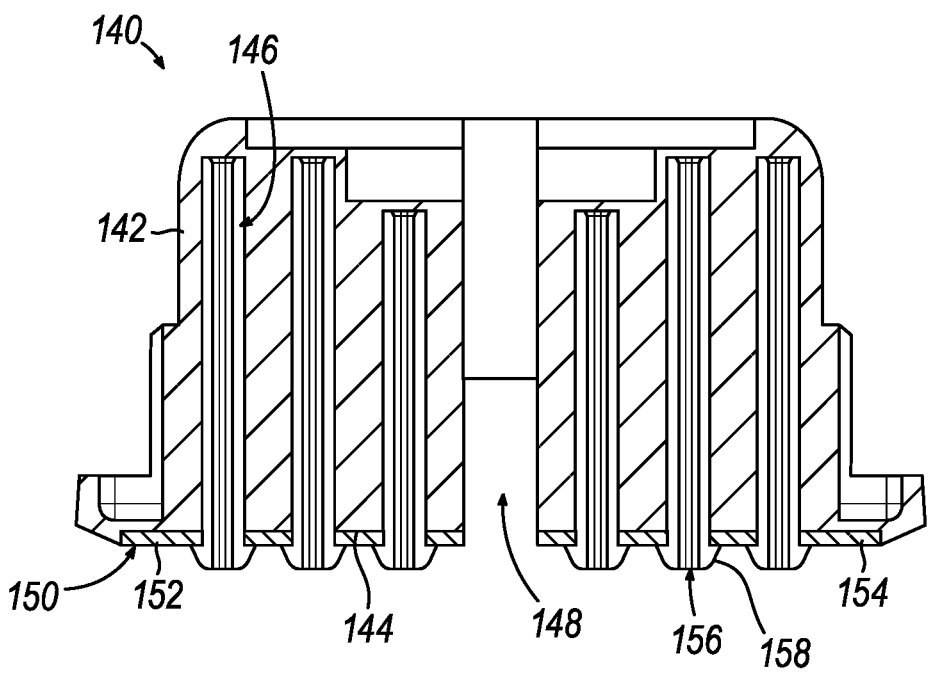
FIG. 13 depicts a front cross-sectional view of the staple cartridge of FIG. 12.

FIGS. 12-13 show an alternative cartridge body assembly (140) that may be readily incorporated into staple cartridge (37) in replacement of cartridge body (70) described above. Therefore, cartridge body assembly (140) may selectively couple to tray (74) to form a staple cartridge configured to selectively couple with lower jaw (16).Cartridge body assembly (140) may be substantially similar to cartridge body (70) described above, with differenced described herein.

Cartridge body assembly (140) includes a 3D printed body (142) and a metal deck (150). 3D printed body (142) may be substantially similar to cartridge body (70) described above, but with differences elaborated below. 3D printed body (142) defines a vertical slot (148) and a plurality of staple apertures (146), which may be substantially similar to vertical slot (49) and staple apertures (51) described above. Rather than having a staple deck, 3D printed body (142) includes an intermediate top surface (44) configured to couple with metal deck (150).

Metal deck (150) includes a first deck surface (152) and a second deck surface (154), which in the current aspect of the disclosure, are completely separate pieces. Each deck surface (152, 154) is configured to couple with a respective side of intermediate top surface (144) such that metal deck (150) and 3D printed body (142) still suitably define vertical slot (148). Each deck surface (152, 154) defines a plurality of staple apertures (156) configured to suitably align with a respective staple aperture (146) of 3D printed body (142). Therefore, staples (47) may be fired through deck surfaces (152, 154) via apertures (156). Each deck surface (152, 154) also includes tissue engagement features (158) adjacent to staple apertures (156), although this is merely optional.

Metal deck (150) may be attached to 3D printed body (142) via any suitable means as would be apparent to one skilled in the art in view of the teachings herein. For example, 3D printed body (142) may be directly 3D printed onto metal deck (150) such that metal deck (150) is the base surface during manufacturing of body (142). Therefore, as 3D printed body (142) is created, metal deck (150) is attached to body (142). As another exemplary means of attachment, metal deck (150) may be applied to 3D printed body (142) via welding, an adhesive material, or a mechanical coupling feature such as a snap fit feature.

3D printed body (142) may be 3D printed using a suitable prototyping material that is easy to produce accurate dimensions in a fast and efficient manner, such as SLA materials used in 3D printing. As mentioned above, use of such a material may not provide sufficient structural integrity to be used in accordance with the description herein. However, metal deck (150) is sufficiently stiff and rigid such that metal deck (150) distribute as least some of the load in response to cartridge body (140) grasping tissue such that an undesirable amount of the tissue grasping forces are not directly imparted on 3D printed body (142). Therefore, in instances where 3D printed body (142) is made from a prototyping material that may be prone to deformation, cracking, or breaking during exemplary use of end effector (12), metal deck (150) may absorb at least some of the tissue grasping forces to inhibit such undesirable consequences.

As a result, the structure of metal deck (150) may allow for 3D printed body (142) to be manufactured with a prototyping material to provide a quick lead time for producing a prototype cartridge body (140).

Figure 14:
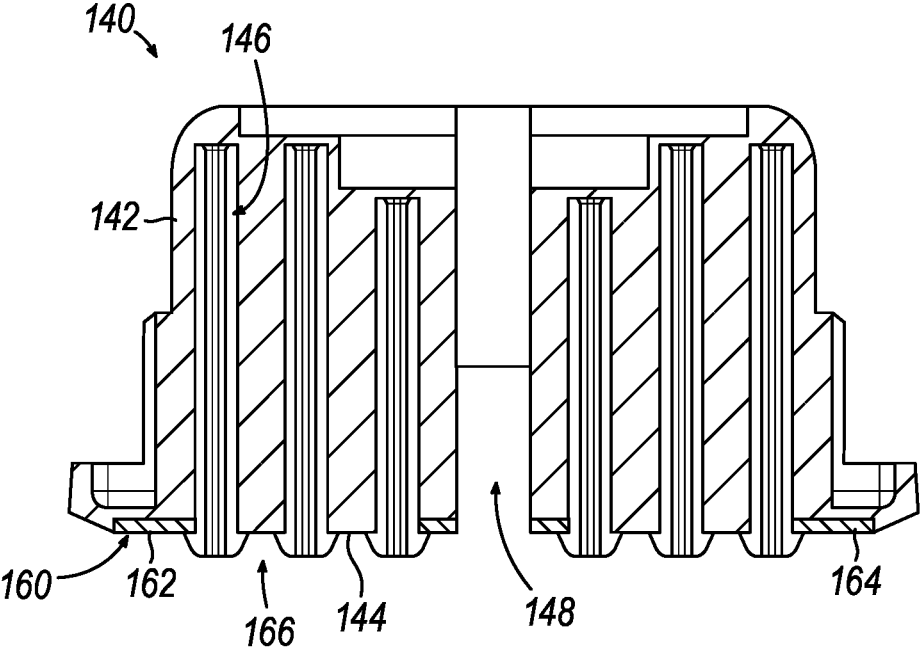
FIG. 14 depicts a front-cross-sectional view of another exemplary staple cartridge having the 3D printed body of FIG. 12 and an alternative exemplary metal deck.

FIG. 14 shows another exemplary metal deck (160) that may be substantially similar to metal deck (150) described above, except metal deck (160) does not define apertures or include tissue engagement features. Therefore, metal deck (160) comprise a first and second deck surface (162, 164) defining a window (166), which may be substantially similar to window (126) described above.

Figure 15:
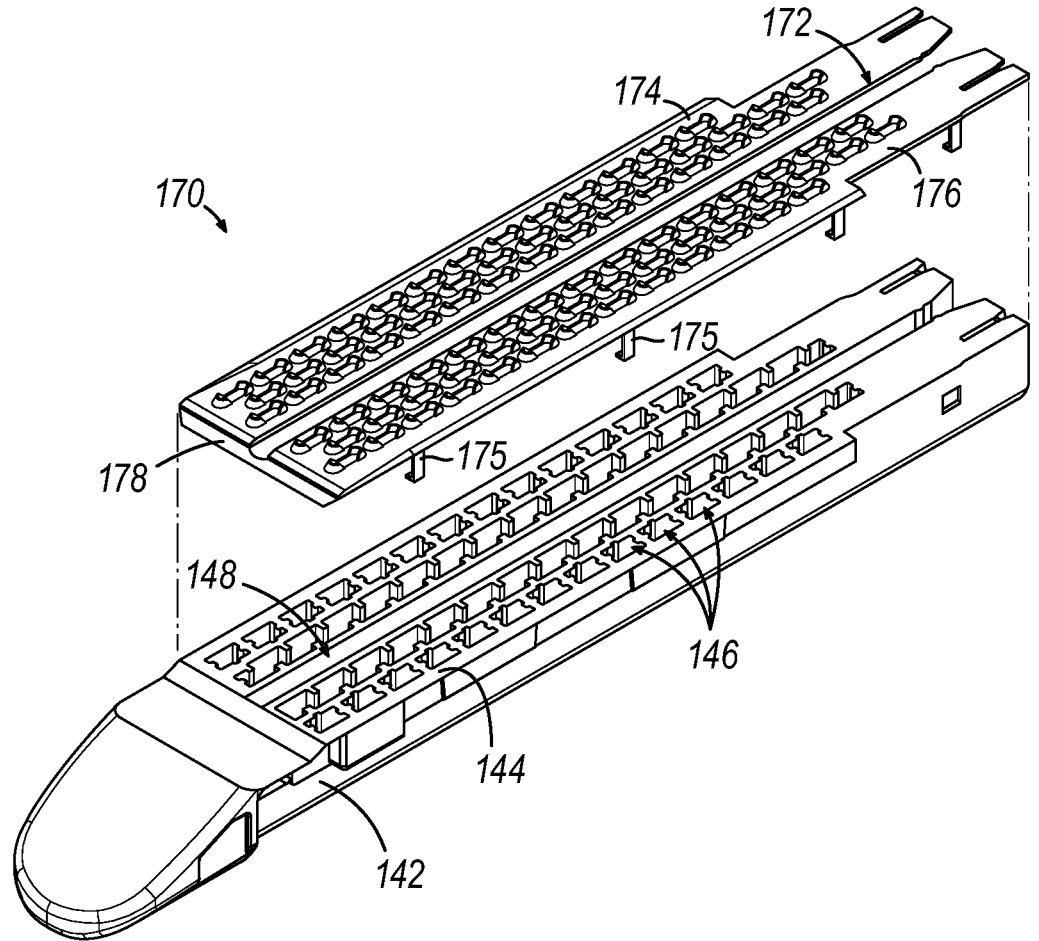
FIG. 15 depicts a perspective view of another exemplary staple cartridge having a 3D printed body and a metal deck.

In the previous examples, metal deck (150) includes two separate pieces (152, 154). However, it should be understood metal deck (150) may be one unitary piece. FIG. 15 shows an exemplary cartridge body assembly (170) formed from 3D printed body (142) described above and a metal deck(172). Metal deck (172) is substantially similar to metal deck (150) described above, with differences elaborated below. Therefore, metal deck (172) includes a first deck surface (174), second deck surface (176), apertures, and tissue engagement features; which may are substantially similar to first deck surface (152), second deck surface (154), apertures (156), and tissue engagement features (158) described above, with differences elaborated below.

In particular, deck surfaces (174, 176) are coupled together with a distal coupling member (178) such that deck surface (174, 176) together define a slot (172) configured to align with slot (148) of 3D printed body (142). Additionally deck surfaces (174, 176) include snap fit features (175) configured to mechanically couple metal deck (172) with 3D printed body (142). Therefore, distal coupling member (178) keeps deck surfaces (174, 176) fixed relative to each other, while snap fit features (175) may be utilized to couple metal deck (172) to body (142).

Figure 16:
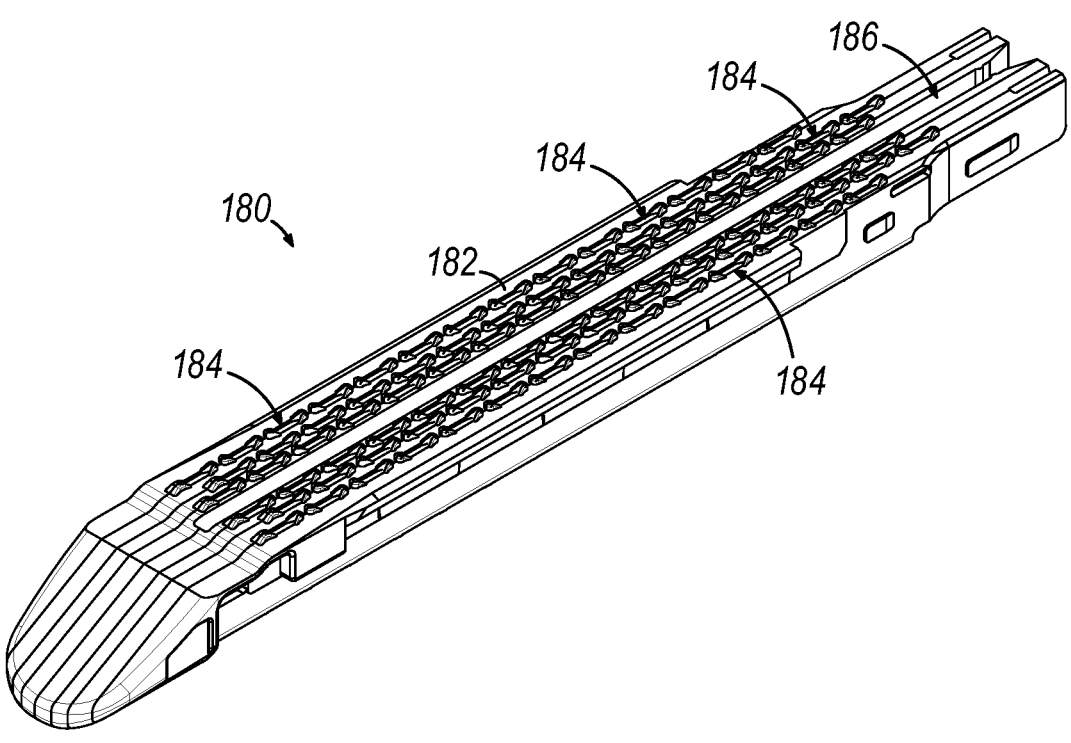
FIG. 16 depicts a perspective view of another exemplary staple cartridge body formed from a plurality of longitudinal sections.
Figure 17:
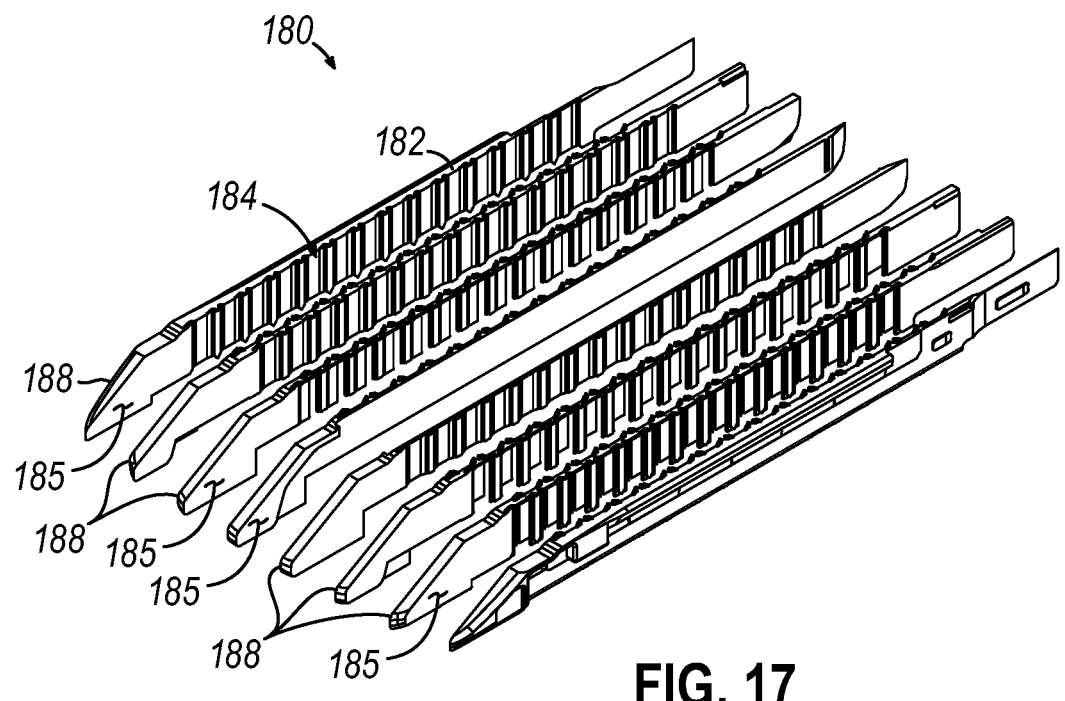
FIG. 17 depicts an exploded perspective view of the staple cartridge body of FIG. 16.
Figure 18:
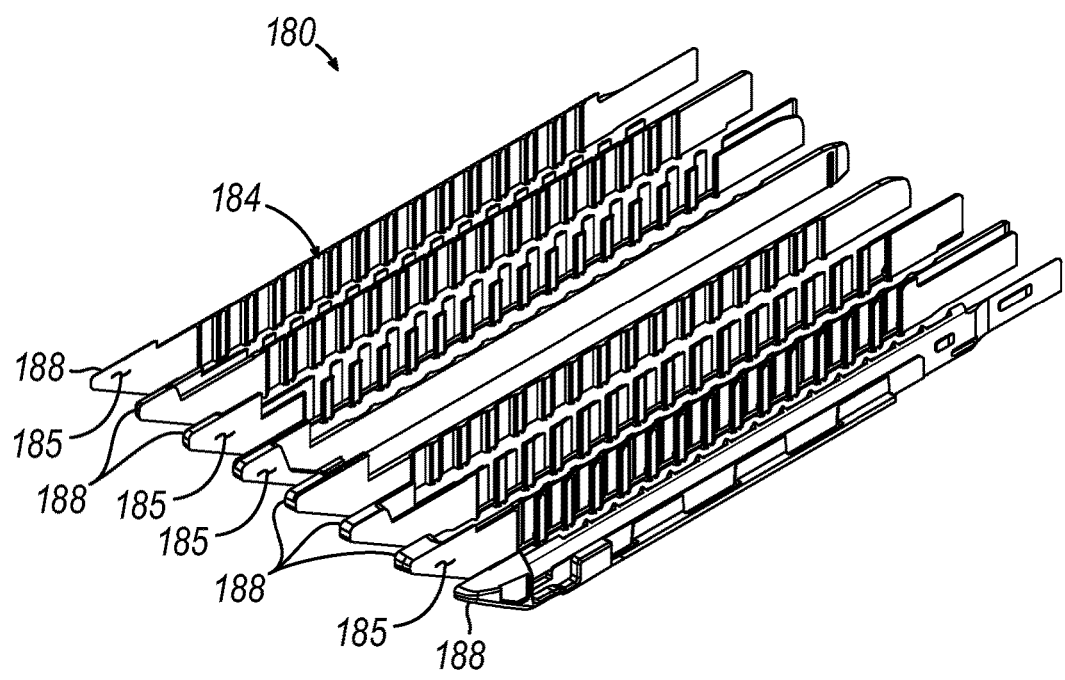
FIG. 18 depicts another exploded perspective view of the staple cartridge body of FIG. 16.

FIG. 16 shows another example cartridge body (180) that may be readily incorporated in replacement of cartridge body (70) described above. Cartridge body (180) is substantially similar to cartridge body (70) describe above, with differences belabored below. Therefore, cartridge body (180) includes a staple deck (182), a plurality of staple apertures (184), and a vertical slot (186); which are substantially similar to staple deck (72), apertures (51), and vertical slot (49) describe above, with differences elaborated below.

Cartridge body (180) is formed from a plurality of longitudinally extending sections (188) each having interior surfaces (185). Longitudinally extending sections (188) may be formed into suitably shapes such that when sections (188) are stacked onto each other and fixed together, sections (188) together form the general shape of cartridge body (180). Sections (188) may be formed of any suitable material as would be apparent to one skilled in the art in view of the teachings herein. Sections (188) may be fixed together for form the general shape of cartridge body (180) utilizing any suitable means as would be apparent to one skilled in the art in view of the teachings herein. For example, sections (188) may be welded together, coupled together via an adhesive material, etc.

Prior to fixed sections (188) together, interior surface (185) of each section (188) may be machined to remove material such that when sections (188) are stacked onto each other, apertures (184), vertical slot (186), and any other suitable features desirable for the proper functioning of cartridge body (180) are formed. As a mere example, interior surfaces (185) may have material removed via wire EDM (Electrical Discharge Machining) to form such features. Having the ability to form such features utilizing longitudinal sections (188) that are then stacked together may save time in manufacturing a prototype cartridge body (180).

Figure 19:
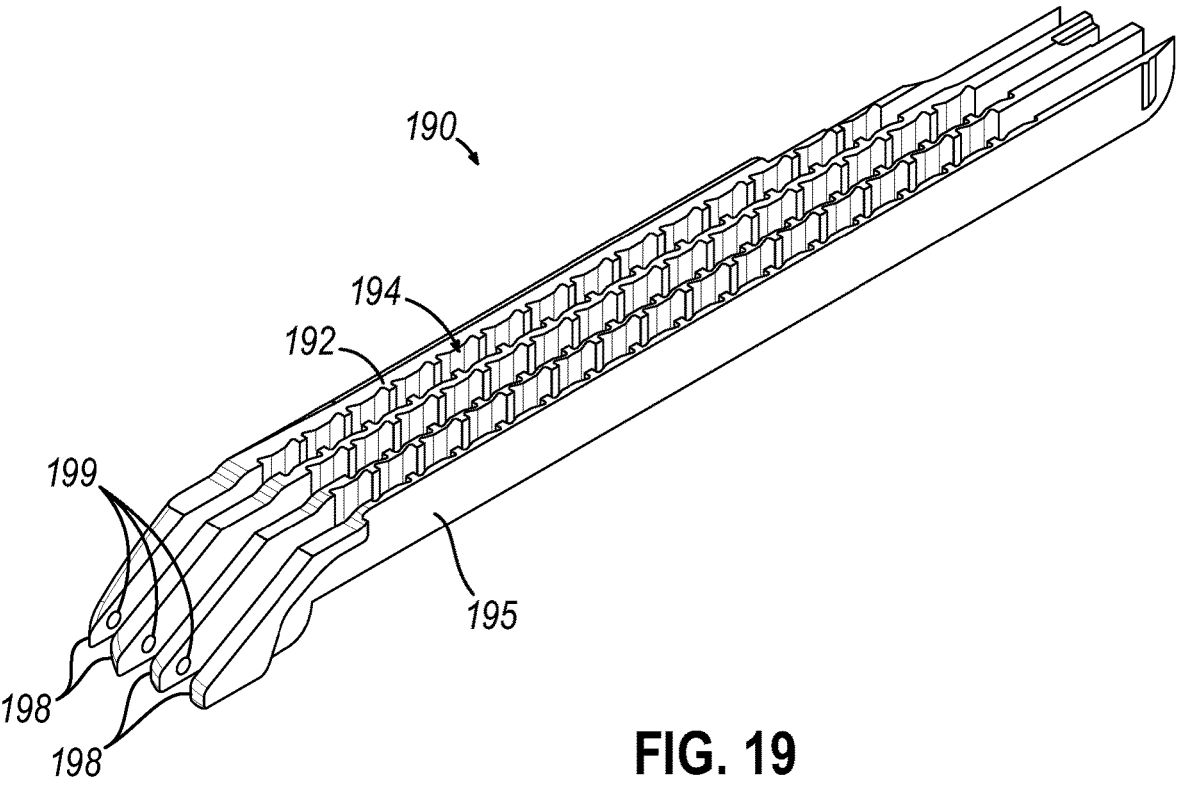
FIG. 19 depicts an exploded perspective view of a portion of an exemplary staple cartridge body formed from a plurality of longitudinal sections.

In some instance, it may be desirable to ensure longitudinal sections (188) are suitably aligned when stacked together such that apertures (184) are suitably aligned across various longitudinal sections (188). FIG. 19 shows an exemplary cartridge body (190) that is substantially similar to cartridge body (180) described above, with alignment features (199) configured to couple with alignment features (199) of adjacent section (198) to ensure sections (198) are suitably oriented relative to each other while stacked together. Therefore cartridge body (190) includes a deck surface (192), staple apertures (194), a vertical slot, and sections (198); which are substantially similar to deck surface (182), staple apertures (184), vertical slot (186), and sections (188)

Additionally, alignment features (199) are presented on the interior surface (195) of respective sections (198). Alignment features (199) ensure that adjacent sections (198) are longitudinally, laterally, and vertically aligned when stacked together. Alignment features (199) may include complementary pin holes and pins, or any other suitably structures and/or features as would be apparent to one skilled in the art in view of the teachings herein.

III. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a first stapling assembly portion that includes a deck surface extending along a longitudinal axis, wherein the deck surface includes a plurality of staple apertures; (b) a plurality of staples; (c) a plurality of staple drivers configured to drive the plurality of staples through the plurality of staple apertures of the deck surface; and (d) a second stapling assembly portion configured to couple with the first stapling assembly portion, wherein a section of the second stapling assembly portion overlies the deck surface, wherein at least one of the first or second stapling assembly portions includes a first support feature configured to inhibit deflection of the deck surface during stapling.

Example 2

The apparatus of any one or more of the preceding Examples, wherein the first support feature at least partially defines a cavity configured to receive at least a portion of the first stapling assembly portion.

Example 3

The apparatus of any one or more of the preceding Examples, wherein the first stapling assembly portion includes a nose disposed at the distal end.

Example 4

The apparatus of any one or more of the preceding Examples, further comprising a second support feature configured to inhibit deflection of the deck surface during stapling.

Example 5

The apparatus of any one or more of the preceding Examples, wherein the first and second support features collectively define a vertical slot that extends along the longitudinal axis.

Example 6

The apparatus of any one or more of the preceding Examples, wherein the first support feature comprises an interior leg defining a portion of the vertical slot.

Example 7

The apparatus of any one or more of the preceding Examples, wherein the second stapling assembly portion is formed from a metallic material, wherein the first stapling assembly portion is formed from a polymeric material.

Example 8

The apparatus of any one or more of the preceding Examples, wherein the first and second stapling assembly portions are coupled together using an adhesive.

Example 9

The apparatus of any one or more of the preceding Examples, wherein the first stapling assembly portion includes a snap fit coupling.

Example 10

The apparatus of any one or more of the preceding Examples, wherein the first support feature includes first and second legs that are positioned perpendicular relative to the longitudinal axis when the apparatus is in an unfired configuration and positioned parallel relative to the longitudinal axis when the apparatus is in a fired configuration.

Example 11

The apparatus of any one or more of the preceding Examples, wherein the second stapling assembly portion is configured to actuate along the longitudinal axis of the first stapling assembly portion to couple with the first stapling assembly portion.

Example 12

The apparatus of any one or more of the preceding Examples, where the apparatus comprises a staple cartridge that includes the plurality of staples, the first assembly portion, and the plurality of staple drivers.

Example 13

The apparatus of any one or more of the preceding Examples, wherein the first stapling assembly portion comprise a polymer, wherein the second stapling body portion comprises a metal staple deck configured to attach on top of the deck surface of the first stapling assembly portion.

Example 14

The apparatus of any one or more of the preceding Examples, wherein the metal staple deck comprises a snap-fit feature configured to selectively couple with the first stapling assembly portion.

Example 15

The apparatus of any one or more of the preceding Examples, wherein the first stapling assembly portion comprises a 3D printed material.

Example 16

An apparatus comprising: (a) a first stapling assembly portion that includes a longitudinally extending body extending along a longitudinal axis; (b) a plurality of staples; (c) a plurality of staple drivers configured to drive the plurality of staples through the plurality of staple apertures of the deck surface, wherein the longitudinally extending body is configured to at least partially house the plurality of staples and the plurality of staple drivers; and (d) a second stapling assembly portion defining a channel extending along the longitudinal axis between a first open end and a second open end, wherein the second stapling assembly comprises a support structure including: (i) a set of exterior sidewalls, and (ii) a set of interior sidewalls, wherein the set of interior sidewalls define a central knife slot, wherein the support structure is configured to receive the longitudinally extending body via the first open end in order to couple the second stapling assembly portion with the first stapling assembly portion, wherein the support structure is configured to enhance the rigidity of the first stapling assembly portion while coupled together.

Example 17

The apparatus of any one or more of the preceding Examples, wherein the support structure is configured to partially house the plurality of stapled and the plurality of staple drivers in conjunction with the longitudinally extending body.

Example 18

The apparatus of any one or more of the preceding Examples, wherein the first stapling assembly portion comprises a deck surface, wherein the support structure defines a window housing the deck surface.

Example 19

The apparatus of any one or more of the preceding Examples, wherein the first stapling assembly portion comprises a Stereolithography material.

Example 20

A method of manufacturing a staple cartridge assembly, the method comprising:
- (a) forming a cartridge body from a polymer, wherein the cartridge body comprises a staple deck defining a plurality of staple apertures configured to house an array of staples;
- (b) separately forming a reinforcement structure from a metal; and (c) attaching the reinforcement structure to the cartridge body such that the reinforcement structure overlies the staple deck to enhance the rigidity of the cartridge body.

IV. Miscellaneous

Any one or more of the teachings, expressions, embodiments, examples, etc. described herein may be combined with any one or more of the teachings, expressions, embodiments, examples, etc. described in U.S. patent aplication Ser. No. 17/951,602, entitled "Surgical Stapler Cartridge with 3D Printable Features," filed Sep. 23, 2022, issued as U.S. Pat. No. 12,274,437 on Apr. 15, 2025, the disclosure of which is incorporated by reference herein.

The teachings of this application may be applied to anvils of all types of surgical staplers, including endocutters, linear surgical staplers, circular surgical staplers, right angle surgical staplers, and curved surgical staplers, for example. For example, the teachings of this application may be combined with various exemplary linear surgical staplers, such that those shown and described in U.S. Pat. No. 11,045,193, entitled "Anvil Assembly for Linear Surgical Stapler," issued Jun. 29, 2021, the disclosure of which is incorporated by reference herein in its entirety. The teachings of this application may be combined with various exemplary circular surgical staplers, such that those shown and described in U.S. Pat. No. 10,709,452, entitled "Methods and Systems for Performing Circular Stapling," issued Jul. 14, 2020, the disclosure of which is incorporated by reference herein in its entirety. The teachings of this application may be combined with various exemplary right angle surgical staplers, such that those shown and described in U.S. Pub. No. 2020/0337698, entitled "Tissue Cutting Washer for Right Angle Surgical Stapler," published Oct. 29, 2020, issued as U.S. Pat. No. 11,266,403 on Mar. 8, 2022, the disclosure of which is incorporated by reference herein in its entirety. The teachings of this application may be combined with various exemplary curved surgical staplers, such that those shown and described in U.S. application Ser. No. 16/945,042, entitled "Features to Enhance Staple Height Consistency in Curved Surgical Stapler," filed Jul. 31, 2020, issued as U.S. Pat. No. 11,432,815 on Sep. 6, 2022, the disclosure of which is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical staple cartridge, comprising:
(a) a cartridge body extending along a longitudinal axis;
(b) a cartridge tray that at least partially overlies a top surface of the cartridge body;
(c) a deck defined by the top surface of the cartridge body or by the cartridge tray and having a plurality of apertures;
(d) a plurality of staples positioned within the apertures;
(e) a plurality of staple drivers actuatable through the cartridge body to the deck to drive the staples through the apertures in the deck, wherein the cartridge tray is configured to constrain the staple drivers relative to the cartridge body; and
(f) a plurality of protrusions defined by an interior portion of the cartridge tray, wherein the protrusions extend transversely to the deck and a bottom surface of the cartridge body and cooperate to at least partially define an elongate slot configured to slidably receive a knife of the surgical stapler, wherein the protrusions are configured to inhibit deflection of the cartridge tray and the cartridge body when patient tissue is clamped against the deck.

2. The surgical staple cartridge of claim 1, wherein the protrusions at least partially define a cavity configured to receive at least a portion of the cartridge body.

3. The surgical staple cartridge of claim 1, wherein a distal end of the cartridge body includes a nose.

4. The surgical staple cartridge of claim 1, wherein the plurality of protrusions include at least first and second fixed protrusions that are laterally opposed about the longitudinal axis.

5. The surgical staple cartridge of claim 4, wherein each of the first and second fixed protrusions extends continuously between a proximal end and a distal end of the elongate slot.

6. The surgical staple cartridge of claim 5, wherein the first and second fixed protrusions cooperate to define at least an upper portion of the elongate slot that is spaced above a lower portion of the elongate slot adjacent to the bottom surface of the cartridge body.

7. The surgical staple cartridge of claim 5, wherein the plurality of protrusions further include a plurality of movable protrusions that are spaced apart longitudinally along the longitudinal axis and cooperate with the first and second fixed protrusions to define the elongate slot, wherein each of the movable protrusions is movable from a first position to a second position in response to firing of the surgical staple cartridge.

8. The surgical staple cartridge of claim 7, wherein the first and second fixed protrusions overlie the movable protrusions such that the first and second fixed protrusions cooperate to define an upper portion of the elongate slot and the plurality of movable protrusions cooperate to define a lower portion of the elongate slot.

9. The surgical staple cartridge of claim 1, wherein the cartridge tray comprises a metallic material, wherein the cartridge body comprises a polymeric material.

10. The surgical staple cartridge of claim 1, wherein the protrusions include a plurality of movable protrusions that are positioned perpendicular relative to the longitudinal axis when the surgical staple cartridge is in an unfired configuration and positioned parallel relative to the longitudinal axis when the surgical staple cartridge is in a fired configuration.

11. The surgical staple cartridge of claim 1, wherein the cartridge body is substantially rigid and thereby configured to resist compressing when the patient tissue is clamped against the deck.

12. A surgical staple cartridge, comprising:
(a) a cartridge body extending along a longitudinal axis;
(b) a cartridge tray that overlies the cartridge body;
(c) a deck defined by one of the cartridge body or the cartridge tray, wherein the deck includes a plurality of apertures configured to house a plurality of staples;
(d) a plurality of staple drivers actuatable through the cartridge body to the deck to drive the staples through the apertures in the deck, wherein the cartridge tray is configured to constrain the staple drivers relative to the cartridge body;
(e) an elongate slot configured to slidably receive a knife; and
(f) a strut defined by the cartridge tray and at least partially defining the elongate slot, wherein the strut is configured to be driven from an upright position substantially transverse to the longitudinal axis to a downward position substantially parallel with the longitudinal axis when the surgical staple cartridge is fired.

13. The surgical staple cartridge of claim 12, wherein the strut comprises a metal.

14. The surgical staple cartridge of claim 12, further including a plurality of struts that include the strut, wherein the struts are longitudinally spaced apart along the longitudinal axis such that the struts are configured to be successively driven from the upright position to the downward position as the surgical staple cartridge is fired.

15. The surgical staple cartridge of claim 12, further comprising a protrusion defined by the cartridge tray, the protrusion cooperating with the strut to at least partially define the elongate slot and inhibit deflection of the cartridge tray and the cartridge body when patient tissue is clamped against the deck before the surgical staple cartridge is fired.

16. The surgical staple cartridge of claim 15, wherein the protrusion comprises a first protrusion, further comprising a second protrusion defined by the cartridge tray and laterally opposed from the protrusion about the longitudinal axis, wherein the first and second protrusions are configured to cooperate to inhibit deflection of the cartridge body when patient tissue is clamped against the deck before the surgical staple cartridge is fired.

17. A surgical staple cartridge, comprising:
(a) a cartridge body extending along a longitudinal axis and including a deck having a plurality of apertures configured to house a plurality of staples;
(b) an elongate slot that extends along the longitudinal axis and is configured to slidably receive a knife of a surgical stapler; and
(c) a cartridge tray that overlies an underside of the cartridge body and a portion of the deck, wherein the cartridge tray includes a rigid protrusion that depends downwardly from the deck in a direction toward the underside and at least partially defines the elongate slot, wherein the protrusion is configured to inhibit deflection of the cartridge tray and the cartridge body when patient tissue is clamped against the deck.

18. The surgical staple cartridge of claim 17, wherein the protrusion comprises a first protrusion, further comprising a second protrusion defined by the cartridge tray and laterally opposed from the first protrusion within the elongate slot, wherein the second protrusion is configured to cooperate with the first protrusion to inhibit deflection of the cartridge body when patient tissue is clamped against the deck.

19. The surgical staple cartridge of claim 18, wherein the first protrusion comprises a first leg and the second protrusion comprises a second leg laterally opposed from the first leg about the longitudinal axis.

\*  \*  \*  \*  \*